(12) United States Patent
Sweigard et al.

(10) Patent No.: US 7,476,537 B2
(45) Date of Patent: Jan. 13, 2009

(54) THERMOPHILIC HYDROPHOBIN PROTEINS AND APPLICATIONS FOR SURFACE MODIFICATION

(75) Inventors: James A. Sweigard, Elkton, MD (US); Barry Stieglitz, Wynnewood, PA (US)

(73) Assignee: E.I. Du Pont de Nemours, Wilmington, DE (US)

( * ) Notice: Subject to any disclaimer, the term of this patent is extended or adjusted under 35 U.S.C. 154(b) by 1 day.

(21) Appl. No.: 11/788,351

(22) Filed: Apr. 19, 2007

(65) Prior Publication Data

US 2007/0298490 A1    Dec. 27, 2007

Related U.S. Application Data

(62) Division of application No. 10/920,876, filed on Aug. 18, 2004, now Pat. No. 7,241,734.

(51) Int. Cl.
*C07H 21/04*    (2006.01)
(52) U.S. Cl. .................. 435/320.1; 536/23.1
(58) Field of Classification Search ............ None
See application file for complete search history.

(56) References Cited

U.S. PATENT DOCUMENTS

| 6,903,191 | B2 | 6/2005 | de Vocht et al. | |
|---|---|---|---|---|
| 7,241,734 | B2* | 7/2007 | Sweigard et al. | 514/2 |
| 2003/0113454 | A1 | 6/2003 | de Vocht et al. | |
| 2003/0134042 | A1 | 7/2003 | deVocht et al. | |
| 2004/0224137 | A1 | 11/2004 | Rogalska et al. | |
| 2005/0238685 | A1 | 10/2005 | Hektor et al. | |

FOREIGN PATENT DOCUMENTS

| WO | WO 00/58342 A1 | 10/2000 |
|---|---|---|
| WO | WO 01/57076 A1 | 9/2001 |

OTHER PUBLICATIONS

Wessels, J. G. H. Developmental Regulation of Fungal Cell Wall Formation, 1994, Annu. Rev. Phytopathol. 32: pp. 413-437.
Whiteford, J. R., P. D. Spanu, Hydrophobins and the interactions between fungi and plants, 2002, Molec. Plant Pathol. 3: pp. 391-400.
Wessels, J. G.H., Hydrophobins: Proteins that Change the Nature of the Fungal Surface, 1997, Adv. Microbiol. Physiol. 38: pp. 1-45.
Kershaw, M. J., J. Talbot., Hydrophobins and Repellents: Proteins with Fundamental Roles in Fungal Morphogenesis, 1998 Fung. Genet. Biol. 29: pp. 18-33.
Scholtmeijer, K., et al., Fungal hydrophobins in medical and technical applications, Appl. Microbiol. Biotechnol. 56: pp. 1-8.
Nakari-Setala, T., et al., Expression of a Fungal Hydrophobin in the Saccharomyces cerevisiae Cell Wall: Effect on Cell Surface Properties and Immobilization, 2002, Appl. Environ. Microbiol. 68: 3385-3391.
Palomo, J. M. et al., Solid-Phase Handling of Hydrophobins: Immobilized Hydrophobins as a New Tool to Study Lipases, 2003 Biomacromol. 4: pp. 204-210.
Bilewicz. R., et al., Modification of Electrodes with Self-Assembled Hydrophobin Layers, 2002, J. Phys. Chem. B. 105: pp. 9772-9777.
Accession No. AAB07707, *Aspergillus fumigatus*, Sep. 9, 1996.
Accession No. P41746, *Aspergillus fumigatus*, Mar. 15, 2004.
Accession No. P28346, *Emericella nidulans*, Mar. 15, 2004.
Bilewicz et al., 2001; Modification of electrodes with self-assembled hydrophobin layers, J. Phys. Che., 105: 9772-9777.
DeVocht et al., 2000; Structural and functional role of the disulfide bridges in the hydrophobin SC3, J. Biol. Chem . . . 275(37); 28428-28432.
Scholtmeijer et al., 2001; Fungal hydrophobins in medical and technical applications, Appl. Microbio. Biotechnol; 56: 1-8.
Scoltmeijer et al., 2002; Surface modifications created by using engineered hydrophobins, Appl. Environ. Microbiol. , 68(3): 1367-1373.
Van der Vegt et al., 1996; A comparison of the surface activity of the fungal hydrophobin SC3p with those of other proteins, Biophysical Chemistry 57: 253-260.
Wosten et al., 1994; Interfacial self-assembly of a hydrophobin into an amphipathic protein membrane mediates fungal attachment to hydrophobic surfaces, EMBO j. 13(24): 5848-5854.
Janssen et al., 2002: Coating with genetic engineered hydrophobin promotes growth of fibroblasts on a hydrophobic solid, Biomaterials, 23: 4847-4854.

* cited by examiner

*Primary Examiner*—Karen Cochrane Carlson
(74) *Attorney, Agent, or Firm*—S. Neil Feltham

(57) ABSTRACT

The present invention relates to a thermophilic hydrophobin, TT1, or a protein or polypeptide substantially similar thereto, derived from the thermophilic fungus *Talaromyces thermophilus*. The invention further relates to a polynucleotide encoding such hydrophobin, as well as to materials coated with such hydrophobin.

8 Claims, 3 Drawing Sheets

Mature TT1 Protein:

LPNVGPSGKTAHKPHQEPFWPVQQDVTVEQAKAICGE

GNQVACCNEVSYAGDTTEIATGPLAGTLKDLLGGKNG

AKGLGLFDKCSRLNVDLLLGLSSLINQECKQHIACCQG
NEADSSNDLIGLNIPCIALGSLL [SEQ ID NO:1]

FIG. 1

```
AAB07707mature  -LPQHDVNAA GNGVGNKGNA NVRFP----V PDDITVKQAT EKCGDQAQLS
P41746mature    -LPQHDVNAA GNGVGNKGNA NVRFP----V PDDITVKQAT EKCGDQAQLS
P28346mature    LPPAHDSQFA GNGVGNKGNS NVKFP----V PENVTVKQAS DKCGDQAQLS
TT1mature       --------LP NVGPSGKTAH KPHQEPFWPV QQDVTVEQAK AICEGNQVA AAB07707mature  CCNKATYAGD VTDIDEGILA GTLKNLIGGG SGTEGLGLFN QCSKLDLQIP
P41746mature    CCNKATYAGD VTDIDEGILA GTLKNLIGGG SGTEGLGLFN QCSNVDLQIP
P28346mature    CCNKATYAGD TTTVDEGLLS GALSGLIGAG SGAEGLGLFD QCSKLDV---
TT1mature       CCNEVSYAGD TTEIATGPLA GTLKDLLGGK NGAKGLGLFD KCSRLNV---

AAB07707mature  VIGPIQALV  NQKCKQNIAC CQNSPSDASG SLIGLGLPCI ALGSIL    [SEQ ID NO:5]
P41746mature    VIGPIQALV  NQKCKQNIAC CQNSPSDASG SLIGLGLPCI ALGSIL    [SEQ ID NO:6]
P28346mature    AVLIGIQDLV NQKCKQNIAC CQNSPSSADG NLIGVGLPCV ALGSIL    [SEQ ID NO:7]
TT1mature       DLLLGLSSLI NQECKQHIAC CQGNEADSSN DLIGLNIPCI ALGSLL    [SEQ ID NO:1]
```

FIG. 2

THERMOPHILIC HYDROPHOBIN PROTEINS AND APPLICATIONS FOR SURFACE MODIFICATION

This application is a divisional of U.S. patent application Ser. No. 10/920,876, filed Aug. 18, 2004, now U.S. Pat. No. 7,241,734.

FIELD OF THE INVENTION

This invention is in the field of biotechnology. More specifically, this invention pertains to a thermophilic hydrophobin protein and the encoding nucleic acid fragment, as well as its use as a surface coating of materials to provide beneficial properties.

BACKGROUND OF THE INVENTION

Hydrophobins are small, secreted cysteine-rich amphipathic proteins found in fungi. Mature hydrophobin proteins, with secretion signal peptides removed, are generally small proteins that are around 100 amino acids in length. Hydrophobins are characterized by having a pattern of 8 highly conserved cysteines that are positioned within the mature protein in a 1-2-1-1-2-1 pattern (dashes represent variable numbers of amino acids). Pairs of these 8 cysteines form disulfide bonds, resulting in 4 disulfide bonds that are necessary for the proper folding of the protein. Though the 8 cysteines are highly conserved, different hydrophobins are quite variable in their amino acid sequences, some having as little as 11% or less sequence identity (Wessels, J. G. H. 1994 *Annu. Rev. Phytopathol.* 32:413-37). Currently, over 50 hydrophobin sequences from a range of fungal species are known, and are available, for example, through GenBank and the National Center for Biotechnology Information (NCBI; Bethesda, Md.). Many fungal species have several reported hydrophobins. Based on differences in protein primary structure, hydrophobins can be grouped into two distinct groups, Class I and Class II.

Genetic studies have implicated hydrophobins as playing roles in providing fungal surface properties. Some hydrophobins, belonging to Class I, are known to form rodlet protein layers found on fungal surfaces. Rodlet layers are extremely hydrophobic and are responsible for generating fungal surface hydrophobicity. Thus all fungal surfaces including aerial hyphae, fruiting bodies and vegetative spores, e.g., conidia, are coated with the hydrophobic domain of self-assembled hydrophobins exposed to the environment and the hydrophilic domain attached or interacting with the hydrophilic cell wall. Thus some roles of hydrophobins in nature are to allow fungal hyphae to escape into the air from its aqueous environment and search for new food sources and surfaces, to line the internal air spaces in *Schizophyllum commune* fruiting bodies in order to prevent flooding by water of these air channels, and to promote interactions between the fungus and the plant during pathogenicity, either acting as elicitors of plant defense responses or as stealth factors protecting the invading fungus from detection and rejection by the plant (Whiteford, J. R., P. D. Spanu 2002 *Molec. Plant Pathol.* 3: 391-400).

The best characterized Class I hydrophobin, SC3, which is obtained from the fungus *Schizophyllum commune*, has been used to study hydrophobin assembly on surfaces and the resulting changes in surface properties. Two Class II hydrophobins, HFBI and HFBII, isolated from *Trichoderma reesei*, have also been studied. These hydrophobins have been found to be useful as surface coatings to alter the properties of the coated surfaces. The amphipathic properties of hydrophobins, meaning having both hydrophobic and hydrophilic properties, allow them to interact with a wide range of material surfaces. In general, upon contact with either hydrophobic or hydrophilic surfaces, hydrophobin monomers self-assemble to form a film covering the surface. A consequence of hydrophobin film formation is a change in surface wettability. Thus on hydrophobic surfaces such as Teflon® film, a hydrophobin coating can increase hydrophilicity as measured by a decrease in the water contact angle. Conversely, on hydrophilic surfaces hydrophobin coatings can decrease wettability, measured by an increase in the water contact angle. Particularly Class I hydrophobin SC3 from the fungus *Schizophyllum commune* and Class II hydrophobins HFBI and HFBII from *Trichoderma reesei* have been used in coating studies. HFBI and HFBII formed weakly ordered and highly crystalline coatings, respectively, on water surfaces (Sermaa, R. et al. Appl. Crystallography 36:499-502). Properties of different hydrophobins, even among hydrophobins within the same Class, can be quite variable in different coating situations.

The novel properties of hydrophobins, including the ability to self-assemble at interfaces in aqueous solution and under mild conditions, immediately suggest potential applications for these surface active proteins. Some potential applications presented in the literature include:

- use in tissue engineering, particularly in coating of unnatural surfaces with a natural protein to increase the unnatural surface biocompatability, e.g., medical implants and surgical instruments (Wessels, J. G. H. 1997 *Adv. Microbiol. Physiol.* 38: 1-45).
- use in drug delivery, especially the delivery of hydrophilic drugs. Drug oil vesicles coated with a hydrophobin would permit attachment of targeting antibodies to the outside of these vesicles (Wessels, J. G. H. 1997 *Adv. Microbiol. Physiol.* 38: 1-45).
- use in the formation of stable foams in food manufacturing and as a natural surface-active agent in hair products (Wessels, J. G. H. 1997 *Adv. Microbiol. Physiol.* 38: 1-45, Kershaw, M. J., J. Talbot. 1998 *Fung. Genet. Biol.* 29: 18-33).
- use to pattern different molecules on a surface with nanometer accuracy (Scholtmeijer, K., et al. 2001 *Appl. Microbiol. Biotechnol.* 56: 1-8).
- use to bind or immobilize factors on a hydrophobic support, such as yeast cells expressing a hydrophobin in its cell wall (Nakari-Setala, T., et al. 2002 *Appl. Environ. Microbiol.* 68: 3385-3391), and several commercially available lipases (Palomo, J. M., et al. 2003 *Biomacromol.* 4:204-210).
- use to develop novel diagnostic sensors through hydrophobin self-assembly on electrode surfaces (Bilewicz, R., et al. 2002 *J. Phys. Chem.* B. 105: 9772-9777).

Hydrophobins used in previous studies have generally been isolated from the natural fungus in which the hydrophobin was identified. However, the amounts of protein that can be obtained using this method of preparation are inadequate for commercial applications. A successful recombinant DNA technology method would be required to supply adequate amounts of hydrophobin proteins for commercial uses. An example of recombinant hydrophobin expression is in WO 00/058342, where the endogenous HFBI hydrophobin was overexpressed in *Trichoderma reesei*. Using a recombinant DNA technology method also allows the creation of hydrophobin variants that may provide superior properties for use in specific applications.

Methods of treating surfaces with hydrophobins to provide a stable coating have been described. In US20030134042, Teflon® materials were incubated in an SC3 hydrophobin solution at 25° C. and then a heat treatment was applied. A heat treatment of 63° C. or 70° C. in the presence of different detergents at a concentration of 0.1% was required to obtain strong binding of the hydrophobin to the Teflon® surface. Heat treatments at lower temperatures, but above 30° C., in the presence of detergent were partially effective in transitioning the SC3 hydrdphobin to a beta-sheet state deemed necessary for strong binding to hydrophobic surfaces.

Another method of treating surfaces requires pretreatment of the hydrophobin prior to application. In US200301 13454 the disulfide bonds of the SC3 hydrophobin were disrupted by treating with sulphite to add sulfite groups, or with reducing agent followed by a sulfhydryl-protecting agent, or with a reducing agent followed by maintenance in a non-oxidizing environment. The thusly treated hydrophobin was then used to coat Teflon® materials. In a third step the hydrophobin coated material was treated to remove sulfhydryl-protecting groups if present, and with an oxidizing agent to reform disulfide bridges.

There is thus a need for identification of hydrophobins that are useful in the types of applications described above, as well as in additional applications. Also there is a need for the isolation of genes encoding useful hydrophobins such that recombinant DNA technology can be used to produce these hydrophobins in adequate amounts for commercial applications. Further, there is a need for rapid, simple methods of treating surfaces with hydrophobins. Accordingly, Applicants have isolated a DNA sequence encoding a novel hydrophobin from a thermophilic fungus, provided improved methods of surface treatment with the encoded hydrophobin protein, and expanded the variety of material surfaces for hydrophobin coating.

SUMMARY OF THE INVENTION

The present invention concerns isolated polynucleotides comprising a nucleotide sequence encoding a mature thermophillic hydrophobin polypeptide wherein the amino acid sequence of the polypeptide and the amino acid sequence of SEQ ID NO:1, representing mature TT1.

In a first embodiment, the present invention includes an isolated polynucleotide comprising: (a) a nucleotide sequence encoding a thermophillic hydrophobin polypeptide, wherein the polypeptide has an amino acid sequence of at least 80%, 85%, 90%, or 95% sequence identity, based on the Clustal W method of alignment, when compared to SEQ ID NO:1 or (b) a complement of the nucleotide sequence, wherein the complement and the nucleotide sequence consist of the same number of nucleotides and are 100% complementary. The polypeptide preferably comprises the amino acid sequence of SEQ ID NO:1. The nucleotide sequence preferably comprises the nucleotide sequence of SEQ ID NO:2.

In a second embodiment, the present invention includes a vector comprising any of the isolated polynucleotides of the present invention.

In a third embodiment, the present invention concerns a recombinant DNA construct comprising any of the isolated polynucleotides of the present invention operably linked to a secretion signal peptide coding sequence and at least one regulatory sequence.

In a fourth embodiment, the present invention concerns an isolated thermophillic hydrophobin polypeptide, wherein the polypeptide has an amino acid sequence of at least 80%, 85%, 90%, or 95% identity, based on the Clustal W method of alignment, when compared to SEQ ID NO:1. The polypeptide most preferably comprises SEQ ID NO:1.

In a fifth embodiment, the present invention includes a composite structure comprising a polymer material having a thermophilic hydrophobin coating.

In a sixth embodiment, the present invention provides a method of treating the surface of an object with a hydrophobin that is performed at a temperature in the range of greater than 25° C. to about 100° C.

BRIEF DESCRIPTION OF THE FIGURES AND SEQUENCE LISTINGS

The invention can be more fully understood from the following detailed description and the accompanying figures and Sequence Listing which form a part of this application.

FIG. 1 shows the amino acid sequence and 8 cysteine pattern of TT1.

FIG. 2 shows a comparison of the amino acid sequences of mature TT1 (SEQ ID NO:1) and the most closely related hydrophobins (SEQ ID NOs: 5, 6, and 7).

Figure 3:
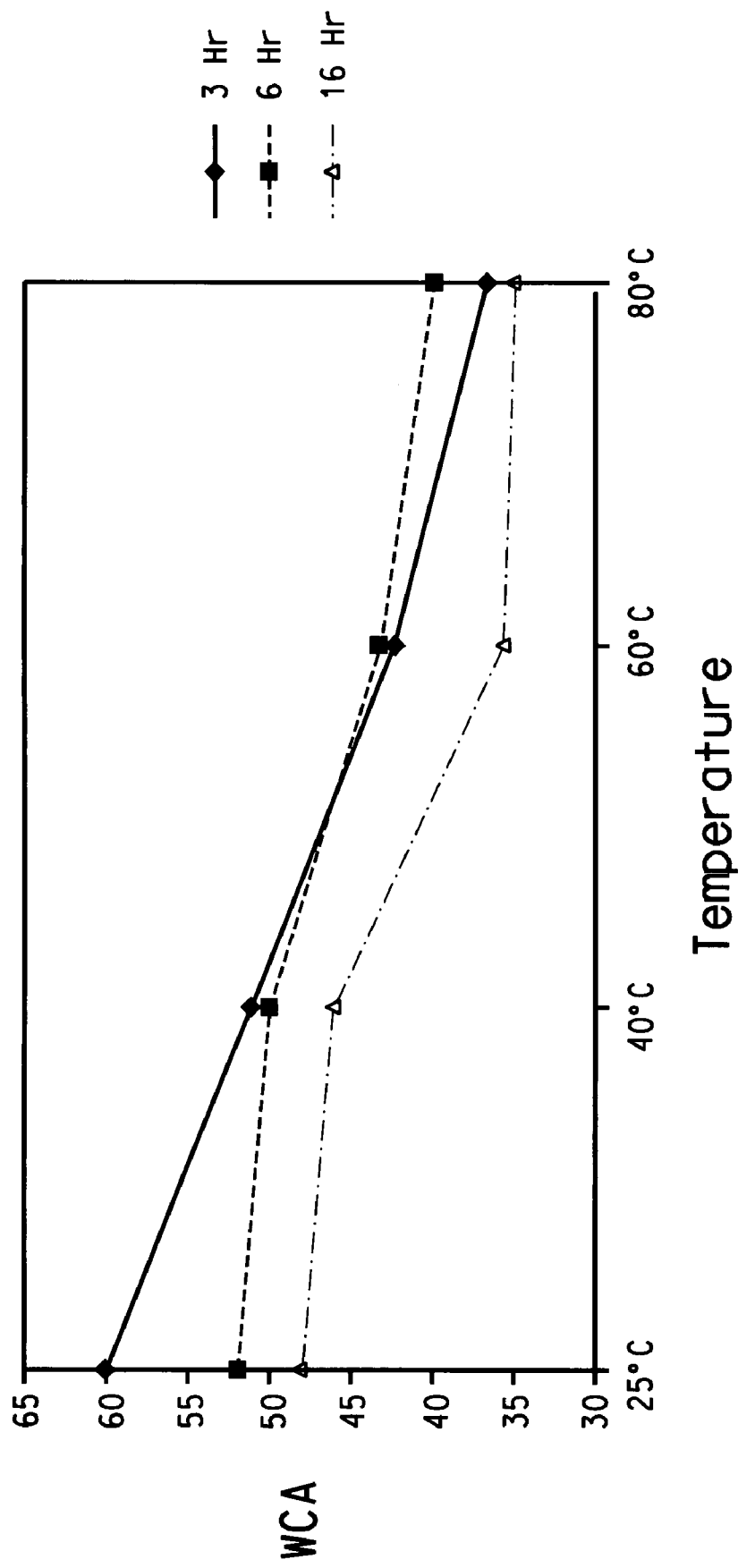
FIG. 3 shows a plot of the water contact angle as a function of time and temperature of hydrophobin treatment of Teflon® PFA.

The invention can be more fully understood from the following detailed description and the accompanying sequence descriptions, which form a part of this application.

The following sequences comply with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the amino acid sequence of the mature TT1 hydrophobin.

SEQ ID NO:2 is the DNA sequence encoding mature TT1 hydrophobin of *Talaromyces thermophilus*.

SEQ ID NO:3 is the amino acid sequence of the precursor TT1 hydrophobin.

SEQ ID NO:4 is the DNA sequence encoding the precursor TT1 hydrophobin of *Talaromyces thermophilus*.

SEQ ID NO:5 is the amino acid sequence of mature HYPL (ACCESSION MB07707), a hydrophobin from *Aspergillus fumigatus*.

SEQ ID NO:6 is the amino acid sequence of mature HYPL (ACCESSION P41746), a hydrophobin rodlet protein from *Aspergillus fumigatus*.

SEQ ID NO:7 is the amino acid sequence of the mature rodlet protein (ACCESSION P28346) of *Emericella nidulans*.

DETAILED DESCRIPTION OF THE INVENTION

The present invention relates to the finding of a polynucleotide encoding a novel hydrophobin named TT1 that was isolated from a thermophilic fungus, *Talaromyces thermophilus*. The TT1 hydrophobin has functional properties relating to its derivation from the thermophilic fungus. There is practical utility for hydrophobins in the coating of various materials to alter their surface properties. In general hydrophobin coating of a material can increase the hydrophobicity of a hydrophilic surface, or increase the hydrophilicity of a hydrophobic surface. The thermophilic TT1 hydrophobin can be applied to surfaces using new methods and provides a coating with increased temperature stability properties.

Most preferred is the polynucleotide encoding the mature TT1 protein and the use of the encoded mature TT1 protein as a polymer surface coating.

Definitions

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 30 contiguous nucleotides, preferably at least 40 contiguous nucleotides, most preferably at least 60 contiguous nucleotides derived from SEQ ID NO:2, or the complement of such sequences.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques. A "recombinant DNA construct" comprises any of the isolated polynucleotides of the present invention operably linked to at least one regulatory sequence.

The "Clustal W method of alignment" corresponds to the alignment method labeled Clustal W (Thompson, J. D., Higgins, D. G. and Gibson, T. J. 1994, Nucleic Acids Research, 22:4673-4680) and found in various bioinformatics computing suites. The "default parameters" are the parameters preset by the manufacturer of the program and as set in the emma program of the emboss suite for multiple alignments they correspond to GAP PENALTY=10 and GAP EXTENSION PENALTY=5, while for pairwise alignments of proteins they are KTUPLE 1, GAP PENALTY=3, WINDOW=5 and DIAGONALS SAVED=5. Defaults for pairwise alignments of nucleic acids are KTUPLE 2, GAP PENALTY=2, WINDOW=4 and DIAGONALS SAVED=4.

As used herein, "substantially similar" refers to nucleic acid fragments wherein changes in one or more nucleotide bases results in substitution of one or more amino acids, but do not affect the functional properties of the polypeptide encoded by the nucleotide sequence. It is therefore understood that the invention encompasses more than the specific exemplary nucleotide or amino acid sequences and includes functional equivalents thereof. The terms "substantially similar" and "corresponding substantially" are used interchangeably herein.

Alterations in a nucleic acid fragment which result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate proteins from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS is increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 70% identical, preferably at least 75% identical to the amino acid sequences reported herein. Preferred nucleic acid fragments encode amino acid sequences that are at least 80% identical to the amino acid sequences reported herein. More preferred nucleic acid fragments encode amino acid sequences that are at least 85-90% identical to the amino acid sequences reported herein. Most preferred are nucleic acid fragments that encode amino acid sequences that are at least 95% identical to the amino acid sequences reported herein. Suitable nucleic acid fragments not only have the above identities but typically encode a polypeptide having at least 50 amino acids, preferably at least 75 amino acids, more preferably at least 90 amino acids, still more preferably at least 100 amino acids, and most preferably at least 125 amino acids.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403-410; see also the explanation of the BLAST alogarithm on the world wide web site for the National Center for Biotechnology Information at the National Library of Medicine of the National Institutes of Health). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a fungal thermophilic hydrophobin protein. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "percent identity", or "sequence identity" as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.) or the AlignX program of Vector NTI v. 7.0 (Informax, Inc., Bethesda, Md.). Multiple alignment of the sequences can be performed using the Clustal method of alignment (Higgins and Sharp, *CABIOS*, 5:151-153 (1989)) with the default parameters (GAP PENALTY=10, GAP LENGTH PENALTY=10). Default parameters for pairwise alignments using the Clustal method are typically KTUPLE 1, GAP PENALTY=3, WINDOW=5 and DIAGONALS SAVED=5.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, recombinant DNA constructs, or chimeric genes. A "transgene" is an isolated nucleic acid fragment or recombinant DNA construct that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different cell types, or at different stages of development, or in response to different environmental conditions. Promoters which cause a nucleic acid fragment to be expressed in most cell types at most times are commonly referred to as "constitutive promoters". New promoters of various types useful to express proteins in expression systems are constantly being discovered. It is further recognized that since in most cases the exact boundaries of regulatory sequences have not been completely defined, nucleic acid fragments of different lengths may have identical promoter activity.

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter).

The term "expression", as used herein, refers to the transcription and accumulation of RNA derived from the nucleic acid fragment of the invention. Expression may also refer to translation of mRNA into a polypeptide "Overexpression" refers to the production of a gene product in transgenic organisms that exceeds levels of production in normal or non-transformed organisms.

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals and secretion signals.

The term "signal peptide" refers to an amino terminal polypeptide preceding the secreted mature protein. The signal peptide is cleaved from and is therefore not present in the mature protein. Signal peptides have the function of directing and translocating secreted proteins across cell membranes. Signal peptide is also referred to as signal protein. The signal protein or peptide of the TT1 hydrophobin described herein comprises the first 16 amino acids of the TT1 precursor protein (SEQ ID NO:3).

"Transformation" refers to the transfer of a nucleic acid fragment into a host cell. Host cells containing the transferred nucleic acid fragments are referred to as "transgenic" or "transformed" cells. Thus, isolated polynucleotides of the present invention can be incorporated into recombinant constructs, typically DNA constructs, capable of introduction into a host cell. Such a construct can be a vector that is used to transfer DNA into the host cell genome or a vector that remains as a replicating unit in the host cell. The vector may include a replication system and sequences that are capable of transcription and translation of a polypeptide-encoding sequence in a given host cell. Typically, expression vectors include, for example, one or more cloned genes under the transcriptional control of 5' and 3' regulatory sequences and a dominant selectable marker. Such expression vectors also can contain a promoter regulatory region (e.g., a regulatory region controlling inducible or constitutive, environmentally- or developmentally-regulated, or cell-specific expression), a transcription initiation start site, a ribosome binding site, an RNA processing signal, a transcription termination site, and/or a polyadenylation signal.

"Stable transformation" refers to the transfer of a nucleic acid fragment into a genome of a host organism, and also to the transfer of a plasmid into a host cell that is then stably maintained, usually due to the use of a selection marker. In contrast, "transient transformation" refers to the transfer of a nucleic acid fragment into the nucleus, or DNA-containing organelle, of a host organism resulting in gene expression without integration or stable maintenance. The term "transformation" as used herein refers to both stable transformation and transient transformation.

The terms "recombinant construct", "expression construct" and "recombinant expression construct" are used interchangeably herein. These terms refer to a functional unit of genetic material that can be transformed into a cell to produce an encoded product. Such construct may be used by itself or may be used in conjunction with a vector. If a vector is used, the choice of vector is dependent upon the host cells and the method that will be used to transform host cells as is well known to those skilled in the art.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"Motifs" or "subsequences" refer to short regions of conserved sequences of nucleic acids or amino acids that comprise part of a longer sequence. For example, it is expected that such conserved subsequences would be important for function, and could be used to identify new homologues in plants. It is expected that some or all of the elements may be found in a homologue. Also, it is expected that one or two of the conserved amino acids in any given motif may differ in a true homologue.

"PCR" or "polymerase chain reaction" is well known by those skilled in the art as a technique used for the amplification of specific DNA segments (U.S. Pat. Nos. 4,683,195 and 4,800,159).

"TT1 protein sample" refers to partially purified TT1 protein that is prepared from an expression system in which a polynucleotide encoding mature TT1 is expressed. In addition to TT1 protein, the sample may include other expression host proteins that are not excluded in the purification scheme.

"Thermophilic hydrophobin coating" refers to a covering, on a surface, of a hydrophobin that is originally derived from a thermophilic host. The density of the covering may be variable and may include other proteins in addition to the thermophilic hydrophobin. The thermophilic hydrophobin coating may be prepared from a partially purified thermophilic hydrophobin protein sample. "TT1 coating" is a specific type of thermophilic hydrophobin coating, which also may have variable density and include other proteins in addition to TT1, that co-purify with TT1.

The term "wettability" as it applies to a liquid is defined as the contact angle between a droplet of the liquid in thermal equilibrium on a horizontal surface.

The term "contact angle" or "water contact angle" is a quantitative measure of the wetting of a solid by a liquid. It is defined geometrically as the angle formed by a liquid at the three phase boundary where a liquid, gas and solid intersect.

TT1 Polypeptide of the Invention

In one embodiment, the present invention concerns a hydrophobin polypeptide having an amino acid sequence that is at least 80% identical, based on the Clustal W method of alignment, to a polypeptide of SEQ ID NO:1. The polypeptide of SEQ ID NO:1 was derived from the thermophilic fungus *Talaromyces thermophilus*, ATCC 16461 and is called TT1. This is the first hydrophobin isolated from a thermophilic fungus. Since *Talaromyces thermophilus* is able to grow and function at higher than normal temperatures, the TT1 protein must be effectively functional in the fungus at the higher temperatures. Thermal tolerance of a hydrophobin is a desirable feature for potential surface applications. Analysis of TT1 properties described in Examples 4 and 5 indicated that its characteristics include thermal stability.

The most closely related sequences to TT1 that are publicly known are the hydrophobins of *Aspergillus fumigatus* (Accession #AAB07707 and #P41746) and of *Emericella nidulans* (Accession #P28346). These hydrophobins have amino acid identities to TT1 of 44.1%, 43.4%, and 43.8%, respectively. These amino acid sequence comparisons are based on the mature proteins. Each of these hydrophobins has a precursor form that includes the signal peptide responsible for secretion of the protein, which is removed to produce the mature protein. Since signal peptide sequences can be quite variable, these were removed prior to making the sequence comparisions. Preferred amino acid sequences of the invention are at least about 80%-85% identical to the mature TT1 sequence, where those sequences that are 85%-90% identical are particularly suitable and those sequences that are about 95% identical are most preferred.

TT1 Polynucleotide and Isolation of Substantially Similar Polynucleotides

In another embodiment the present invention concerns an isolated polynucleotide comprising a nucleotide sequence encoding a thermophllic fungal hydrophobin polypeptide having at least 80% identity, based on the Clustal W method of alignment, when compared to SEQ ID NO:1, representing TT1.

This invention also includes the isolated complement of such polynucleotides, wherein the complement and the polynucleotide consist of the same number of nucleotides, and the nucleotide sequences of the complement and the polynucleotide have 100% complementarity.

The nucleic acid fragments of the instant invention may be used to isolate cDNAs and genes encoding homologous proteins from the same or other fungal species. Isolation of homologous genes using sequence-dependent protocols is well known in the art. Examples of sequence-dependent protocols include, but are not limited to, methods of nucleic acid hybridization and methods of DNA and RNA amplification as exemplified by various uses of nucleic acid amplification technologies (e.g., polymerase chain reaction, ligase chain reaction).

For example, genes encoding other hydrophobins that are substantially similar to TT1, either as cDNAs or genomic DNAs, could be isolated directly by using all or a portion of the instant polynucleotide as a DNA hybridization probe to screen libraries from any desired fungus employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic DNA fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding fungal genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673-5677; Loh et al. (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least 30 (preferably at least 40, most preferably at least 60) contiguous nucleotides derived from a nucleotide sequence of SEQ ID NO:2 or SEQ ID NO:4 and the complement of such nucleotide sequences may be used in such methods to obtain a nucleic acid fragment encoding a substantial portion of an amino acid sequence of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

Expression of TT1 Encoding Polynucleotide

The polynucleotides of the instant invention can be used to produce TT1 protein. One skilled in the art will know how to prepare chimeric genes comprising the polynucleotide of the invention that are suitable for expression of the precursor or mature TT1 protein in a production system. Preferred production systems are secretion systems which include, but are not limited to, bacterial expression systems such as *Bacillus* (Nagarajan, V et al. 1992 Gene 114:121-126), yeast expression systems such as *Saccharomyces* and *Pichia*, and fungal systems such as *Trichoderma* (Berquist, P. L. et al. 2004 32:293-7) and *Aspergillis* (Gouka, R. J. et al. 1997 Appl Mictobiol Biotechnol 47:1-11). For expression, the TT1 polynucleotide is operably linked to a promoter that is functional in the desired host, and optionally to other regulatory signal sequences, to produce a chimeric gene. When using the polynucleotide encoding the mature TT1 protein, to direct secretion it is necessary to include operably linked in the chimeric gene a DNA sequence encoding a secretion signal peptide. The secretion signal peptide may be that derived from the precursor TT1 protein, or it may be derived from a heterologous gene. Examples of secretion signal peptides used in *Bacillus* expression systems are described in Nagarajan, V. et al. (1992, Gene 114:121-126). Secretion signal peptides for use in an expression system may be derived from a protein that is secreted in that host, for example, hydrophobin signal peptides may be used for secretion in fungal expression systems.

Various tags may be added to a chimeric gene that result in the expression of a peptide tag attached to the expressed protein. The use of these tags is known to those skilled in the art, for example, for detecting and purifying the expressed protein, since antibodies to the tag peptide or means of adsorbing the tag peptide to a substrate are available. Examples of such tags are the Flag tag and the His tag.

The chimeric gene construction for expression of TT1 in *Trichoderma* contains the following components, in the following order:

1) the promoter from the Trichoderma cbh1 (cellulase) gene
2) the polynucleotide encoding the secretion signal peptide of the cbh1 precursor protein
3) the polynucleotide encoding the mature TT1 protein with no translation stop codon
4) a polynucleotide encoding the Flag octapeptide and a His (6x) tag, incorporated to facilitate screening of fungal transformants and to aid in purification, followed by a translation stop codon
5) the transcription termination sequence from the cbh1 gene Plasmid vectors comprising the TT1 chimeric gene may be constructed for transfer of the chimeric gene into a host. The choice of plasmid vector is dependent upon the selected host and the method that will be used to transform the host cells. Expression vectors containing regulatory sequences-that direct high level expression of foreign proteins, marker genes, and replication origins, if desired, are well known to those skilled in the art. The skilled artisan is well aware of the genetic elements that must be present on the plasmid vector in order to successfully transform, select and propagate host cells containing the recombinant DNA construct or chimeric gene. For example, a selection marker gene may be included, which is used to identify transformants. Transformation of the recombinant DNA vector may result in a plasmid being a transient or replicating stable resident of the host cell, or in integration of all or a segment of the introduced DNA into the host genome. Integration vectors generally include polynucleotides of homologous sequence to the host genome for targeted integration. The skilled artisan will also recognize that different independent integrative stable transformation events will result in different levels of expression and thus that multiple events must be screened in order to obtain lines displaying the desired expression level. Such screening may be accomplished by Southern analysis of DNA, Northern analysis of mRNA expression, Western analysis of protein expression, or phenotypic analysis.

TT1 is preferably produced in a fungal expression system using methods familiar to one skilled in the art as described for *Schizophyllum* in Scholtmeijer, M et al. (2002 Applied and Environmental Microbiology 68: 1367-1373), for *Aspergillis* in Gouka, R. J. et al. (1997 Appl Mictobiol Biotechnol 47:1-11), and for *Trichoderma in* WO2000058342. Transformants containing the chimeric gene construction described above, identified through selection, are grown on cellulose-containing medium to induce expression of the cbh1 gene promoter. Production of TT1 is assayed through immunodetection using an anti-Flag antibody to identify the highest expressing strain. An antibody to TT1 can be prepared to the TT1 polypeptide by methods known to those skilled in the art, which can then serve as an alternative probe for immunodetection of TT1 in transformants.

In a fungal expression host, expression of the endogenous hydrophobin(s) may be blocked so that these endogenous hydrophobin(s) do not co-purify with the production hydrophobin. Endogenous gene expression may be blocked by methods known to those of skill in the art, for example by deleting the encoding gene or a portion of the gene, inserting a blocking sequence into the encoding gene, disrupting the promoter of the encoding gene, expressing an antisense RNA to the endogenous hydrophobin messenger RNA and other such methods. It is preferred that the endogenous HFB II hydrophobin expression is eliminated in the Trichoderma expression host strain for production of TT1.

The expressed TT1 protein may be partially purified using hydrophobin protein purification methods known to those skilled in the art. These methods generally involve the formation of a foam that incorporates the hydrophobin on its surface. The foam may be created by methods such as releasing hydrogen bubbles from a Pt cathode positioned at the bottom of a container with the anode under the surface of the medium (Scholtmeijer et al., 2002, Appl and Envrt. Microbio. 68:1367-1373) and by rapid mixing. The foam sample is harvested and then lyophilized. The sample may be resuspended in trifluoroacetic acid (TFA) which is then removed by evaporation to dryness, and the sample is resuspended in water. An alternative hydrophobin purification method is to adsorb the hydrophobin to a surface, then to solubilize the adsorbed hydrophobin by incubating in a solution containing a surfactant at a temperature lower than 90° C., and to separate the resulting hydrophobin-enriched solution (US20030166960). The partially purified hydrophobin can be used in materials coating applications as described below. Alternatively, one of skill in the art will recognize that further purified TT1 protein may be prepared using the His tag, a TT1 antibody, or other protein purification methods known to those skilled in the art. The % of TT1 protein in the TT1 protein sample is preferred to be between about 10% and about 100%.

Novel Properties of TT1

The native organism from which TT1 was discovered is the thermophilic fungus, *Talaromyces thermophilus*, which grows at 45° C. Being derived from a thermophilic fungus, TT1 can therefore be classified as a thermophilic hydrophobin. Thermal stability properties of TT1 could be apparent in applications of TT1, and Applicants have shown that this is the case. As demonstrated in the examples below, TT1 coated a surface better at temperatures that are higher than room temperature, and the coating was stable to a 24 hour 90° C. treatment when the coating was applied at those higher temperatures. In addition, the use of elevated temperatures during coating improved the coating rate and extent. Thus applications of TT1 in materials coatings can take advantage of thermal stability properties of TT1 to provide enhanced coating application to surfaces and coating stability on surfaces.

Thermophilic hydrophobins are considered to be those hydrophobins present in thermophilic fungi. Other thermophilic hydrophobins may vary substantially in primary amino acid sequence from that of TT1, but may retain thermophilic properties as demonstrated for TT1. Such a thermophilic hydrophobin may be substituted for TT1 in the methods and applications described herein.

Materials and Treatments for Coatings of TT1

TT1 is useful for coating a wide variety of materials for altering surface properties related to hydrophobicity and hydrophilicity, particularly polymeric materials. Such materials may be in the form of, for example, films, sheets, fibers, woven and nonwoven fabrics, particles, or molded articles. They may also contain any additives known in the art, such as, but not limited to, glass or mineral fillers, carbon fibers, flame retardants, pigments, stabilizers, and the like. The polymeric materials may be present as one or more components in blends or composites with other materials. Examples of polymers suitable for use in the present invention include, but are not limited to, fluoropolymers, polyolefins, and polyesters.

Fluoropolymers suitable for use in the present invention include, but are not limited to, homopolymers and copolymers comprising one or more of the following monomers: tetrafluoroethylene (TFE), vinyl fluoride, trifluoroethylene, vinylidene fluoride, chlorotrifluoroethylene, hexafluoropropylene, hexafluoroisobutylene, perfluoro methyl vinyl ether, 4,5-difluoro-2,2-bis(trifluoromethyl)-1,3-dioxole, perfluoro (2-methylene-4-methyl-1,3-dioxolane, and perfluoro vinyl ethers such as perfluoro propyl vinyl ether and perfluoro methyl vinyl ether. Examples of commercially available fluoropolymers suitable for use in the present invention include, but are not limited to, those sold under the trademarks Teflon®, Tedlar®, and Nafion® by E. I. du Pont de Nemours & Co., Inc. (Wilmington, Del.).

Polyolefins suitable for use in the present invention include olefinic homopolymers such as polypropylene and polyethylene, including such polyethylenes as low density polyethylene (LDPE), very low density polyethylene (VLDPE), linear low density polyethylene (LLDPE), high density polyethylene (HDPE), ultra low density polyethylene(ULDPE), metallocene-catalyzed polyethylene, high performance polyethylene (HPPE), and ultra high molecular weight polyethylene (UHMWPE). Also included as polyolefins in the present invention are ethylene copolymers, including but not limited to, copolymers of ethylene and vinyl esters such as vinyl acetate, and copolymers of ethylene and unsaturated acid or esters of those acids such as acrylic or methacrylic acid, or 1-8 carbon alkyl acrylates and methacrylates, or mixtures of these comonomers. Also included are ionomers of ethylene/acrylic acid or methacrylic acid copolymers and terpolymers. Ionomers are the well known metal ion partially neutralized ethylene/(meth)acrylic acid copolymers, described in U.S. Pat. No. 3,264,272 (Rees) which is hereby incorporated by reference.

Also included as polyolefins in the present invention are graft copolymers such as those described in U.S. Pat. No. 4,026,967, in which the graft monomers include thermally stable unsaturated carboxylic anhydrides and dianhydrides, and the backbone polymers are preferably polymers of ethylene and copolymers derived from ethylene and $C_3$-$C_8$ alpha-olefins, including copolymers of at least one olefin with other monomers. Examples of suitable graft monomers include methacrylic acid, acrylic acid, glycidyl methacrylate, 2-hydroxy ethylacrylate, 2-hydroxy ethyl methacrylate, diethyl maleate, monoethyl maleate, di-n-butyl maleate, maleic anhydride, maleic acid, fumaric acid, itaconic acid, dodecenyl succinic anhydride, 5-norbornene-2,3-anhydride, and nadic anhydride (3,6-endomethylene-1,2,3,6-tetrahydrophthalic anhydride). Fumaric acid, maleic anhydride, and glycidyl methacrylate are particularly preferred graft monomers. Examples of suitable backbone polymers are polyethylene, e.g., high density polyethylene (HDPE), low density polyethylene (LDPE), linear low density polyethylene (LLDPE), metallocene-catalyzed polyethylene, very low density polyethylene (VLDPE), Ultra Low Density Polyethylene (ULDPE), ultrahigh molecular weight polyethylene (UHMWPE), high performance polyethylene (HPPE); copolymers derived from ethylene and at least one monomer chosen from propylene, methyl acrylate, ethyl acrylate, n-butyl acrylate, methyl methacrylate, acrylic acid, methacrylic acid and carbon monoxide; and copolymers of olefins with a diolefin, such as a copolymer of ethylene, or of ethylene and other olefins, such as propylene, with: linear aliphatic nonconjugated dienes of at least six carbon atoms (such as 1,4-hexadiene) and other dienes, conjugated or not, such as norbornadiene, dicyclopentadiene, ethylidene norbornene, butadiene, and the like.

Also included are blends comprising at least one polyolefin. Examples of polyolefins suitable for use in the present invention include, but are not limited to, Bynel® adhesive resins, Elvaloy® modifier resins, Elvaloy® AC acrylate copolymer resins, Elvanol® polyvinyl alcohol, Elvax® vinyl acetate copolymer resins, Fusabond® modifier resins, Nucrel® acid copolymer resins, Surlyn® ionomer resins, Tyvek® spunbonded polyolefin sheet from E. I. du Pont de Nemours & Co., Inc. (Wilmington, Del.) and ATTANE™ ULDPE Resins, DOW LDPE Resins, DOW LLDPE Resins, DOWLEX™ PE Resins, ELITE™ EPE Resins, FLEXOME™ VLDPE Resins, PRIMACOR™ Copolymers, TUFLIN™ LLDPE Resins and DOW Polypropylene Resins from the Dow Chemical Company (Midland, Mich.).

Polyesters comprise those polymers prepared from diols and dicarboxylic acids. Dicarboxylic acids useable in the preparation of polyesters suitable for use in the present invention include, but are not limited to, unsubstituted and substituted aromatic, aliphatic, unsaturated, and alicyclic dicarboxylic acids and the lower alkyl esters of dicarboxylic acids having from 2 carbons to 36 carbons. Specific examples of the desirable dicarboxylic acid component include terephthalic acid, dimethyl terephthalate, isophthalic acid, dimethyl isophthalate, 2,6-napthalene dicarboxylic acid, dimethyl-2,6-naphthalate, 2,7-naphthalenedicarboxylic acid, dimethyl-2,7-naphthalate, 3,4'-diphenyl ether dicarboxylic acid, dimethyl-3,4'diphenyl ether dicarboxylate, 4,4'-diphenyl ether dicarboxylic acid, dimethyl-4,4'-diphenyl ether dicarboxylate, 3,4'-diphenyl sulfide dicarboxylic acid, dimethyl-3,4'-diphenyl sulfide dicarboxylate, 4,4'-diphenyl sulfide dicarboxylic acid, dimethyl-4,4'-diphenyl sulfide dicarboxylate, 3,4'-diphenyl sulfone dicarboxylic acid, dimethyl-3,4'-diphenyl sulfone dicarboxylate, 4,4'-diphenyl sulfone dicarboxylic acid, dimethyl-4,4'-diphenyl sulfone dicarboxylate, 3,4'-benzophenonedicarboxylic acid, dimethyl-3,4'-benzophenonedicarboxylate, 4,4'-benzophenonedicarboxylic acid, dimethyl-4,4'-benzophenonedicarboxylate, 1,4-naphthalene dicarboxylic acid, dimethyl-1,4-naphthalate, 4,4'-methylene bis(benzoic acid), dimethyl-4,4'-methylenebis(benzoate), oxalic acid, dimethyl oxalate, malonic acid, dimethyl malonate, succinic acid, dimethyl succinate, methylsuccinic acid, glutaric acid, dimethyl glutarate, 2-methylglutaric acid, 3-methylglutaric acid, adipic acid, dimethyl adipate, 3-methyladipic acid, 2,2,5,5-tetramethylhexanedioic acid, pimelic acid, suberic acid, azelaic acid, dimethyl azelate, sebacic acid, 1,11-undecanedicarboxylic acid, 1,10-decanedicarboxylic acid, undecanedioic acid, 1,12-dodecanedicarboxylic acid, hexadecanedioic acid, docosanedioic acid, tetracosanedioic acid, dimer acid, 1,4-cyclohexanedicarboxylic acid, dimethyl-1,4-cyclohexanedicarboxylate, 1,3-cyclohexanedicarboxylic acid, dimethyl-1,3-cyclohexanedicarboxylate, 1,1-cyclohexanediacetic acid, metal salts of 5-sulfodimethylisophalate, fumaric acid, maleic anhydride, maleic acid, hexahydrophthalic acid, phthalic acid and the like and mixtures derived therefrom.

Diols useful in the preparation of polyesters suitable for use in the present invention include, but are not limited to, unsubstituted, substituted, straight chain, branched, cyclic aliphatic, aliphatic-aromatic or aromatic diols having from 2 carbon atoms to 36 carbon atoms. Specific examples of the desirable diol component include ethylene glycol, 1,3-propanediol, 1,2-propanediol, 1,2-, 1,3- and 1,4-butanediol, 1,5-pentane diol, 1,6-hexanediol, 1,8-octanediol, 1,10-decanediol, 1,12-dodecanediol, 1,14-tetradecanediol, 1,16-hexadecanediol, dimer diol, isosorbide, 4,8-bis(hydroxymethyl)-tricyclo [5.2.1.0/2.6]decane, 1,2-, 1,3- and 1,4-cyclohexanedimethanol, and the longer chain diols and polyols made by the reaction product of diols or polyols with alkylene oxides including di(ethylene glycol), tri(ethylene glycol), poly(ethylene ether) glycols, poly(butylene ether) glycols and the like and mixtures derived therefrom.

The preferred polyesters useful herein are poly(ethylene terephthalate), poly(trimethylene terephthalate), and blends and copolymers thereof. Such polyesters are sold, for example, under the trademarks Rynite®, Sorona®, (both E. I. du Pont de Nemours & Co., Inc., Wilmington, Del.), Dacron® (Invista, Koch Industries, Wichita, Kans.), and Mylar®. (DuPont Teijin Films, Hopewell, Va.).

Materials that are hydrophilic in nature such as glass and mica may be coated with TT1 to increase hydrophobicity. A preferable increase in hydrophobicity is measured as an increase in water contact angle of about 20° following coating. Materials that are hydrophobic in nature may be coated with TT1 to increase hydrophilicity. Preferred materials for TT1 coating to increase hydrophilicity are materials such as Teflon® and Tedlar® fluoropolymers, polyolefins such as Tyvek®, Bynel®, Surlyn®, polypropylene and low density polyethylene (LDPE), and polyesters such as Sorona® (demonstrated in Example 3), as well as related materials. Materials with a water contact angle of about 70° or higher are preferred.

When treated with TT1 protein sample these materials showed altered surface properties as measured by the water contact angle (WCA) (Rouxhet, P. G. et al., "Chemical composition and physico-chemical properties of polymer surfaces" Progress in Organic Coatings (1993), 22(1-4), 327-44). The measured reduction in WCA indicated that the surface was more hydrophilic following TT1 protein sample treatment. The increased hydrophilicity may be a valuable property in such applications as in biomaterials, drug delivery systems, and in the coating of materials used for contact lenses. Materials that have a change in WCA ($\Delta C$) following TT1 protein sample treatment of at least about 20° are preferred, those with a $\Delta C$ of at least about 30° are more preferred, and those with a $\Delta C$ equal to or greater than 40° are most preferred.

An object that may be treated with TT1 protein sample is one that contains one or more materials that undergo a water contact angle change of at least 20° when so treated. Such an object may include and is not limited to a medical device, an electronic device, a container including a bottle, a tray and an assay plate, a particle, a window, and an object that includes a lens. Any object that includes a material where it is desirable to change (reduce or enhance, depending on the hydrophobic or hydrophilic nature of the starting material) the water contact angle of that material can be treated with TT1 protein sample. Treatment includes the application of TT1 through contact with a solution comprising TT1. Contact may be by any method such as by dripping a TT1 comprising solution onto a material, spraying a TT1 comprising solution onto a material, and by immersing a material in a TT1 comprising solution. Preferred treatment is within a temperature range of greater than 25° C. to about 100° C. Another embodiment is treatment within a temperature range of equal to or greater than 30° C. to about 100° C., and an additional embodiment is treatment within a temperature range of equal to or greater than 35° C. to about 100° C. Additional embodiments are treatments within temperature ranges each having a lower limit of a previous embodiment, and each with an upper limit of the range at about 80° C., i.e. >25° C. to about 80° C., >/=30° C. to about 80° C., >/=35° C. to about 80° C. Treatment is preferably applied without using detergent in the TT1 comprising solution.

Thermophilic hydrophobin coatings may have different degrees of stability to different types of treatments. The degree of stability to a specific set of conditions that is required may vary depending on the specific application of the coated material. Some examples of different conditions under which stability can be assessed are washing with warm water, heating to 90° C.-100° C. for 10 minutes in a detergent solution, and abrasion. A change in water contact angle of preferably less than 15° is an indication of stability. Preferable are composite structures comprising a polymer material with a thermophilic hydrophobin coating that are stable to warm water washing, such as TT1 coated Teflon® PFA. More preferred are composite structures that are stable to all three conditions above such as TT1 coated Sorona® 3GT.

A TT1 coating may be any amount of TT1 protein sample that is retained on a material surface such that the water contact angle of that surface is changed by at least about 200. Additional proteins that co-purify with TT1 may be included in the TT1 coating.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The meaning of abbreviations used is as follows: "min" means minute(s), "hr" means hour(s), "µL" means microliter(s), "mL" means milliliter(s), "L" means liter(s), "nm" means nanometer(s), "mm" means millimeter(s), "cm" means centimeter(s), "µm" means micrometer(s), "mM" means millimolar, "M" means molar, "mmol" means millimole(s), "µmole" means micromole(s), "g" means gram(s), "µg" means microgram(s), "mg" means milligram(s), "g" means the gravitation constant, "rpm" means revolutions per minute, "kb" means kilobase(s), "bp" means base pairs, "$OD_{600}$" means the optical density measured at 600 nm, "$OD_{260}/OD_{280}$" means the ratio of the optical density measured at 260 nm to the optical density measured at 280 nm.

General Methods:

Standard recombinant DNA and molecular cloning techniques used in the Examples are well known in the art and are described by Sambrook, J., Fritsch, E. F. and Maniatis, T., *Molecular Cloning: A Laboratory Manual*, Cold Spring Harbor Laboratory Press, Cold Spring Harbor, N.Y., 1989, by T. J. Silhavy, M. L. Bennan, and L. W. Enquist, *Experiments with Gene Fusions*, Cold Spring Harbor Laboratory, Cold Spring Harbor, N.Y., 1984, and by Ausubel, F. M. et al., *Current Protocols in Molecular Biology*, Greene Publishing Assoc. and Wiley-lnterscience, N.Y., 1987.

Example 1

Identification of Novel Hydrophobin from *Talaromyces thermophilus*

A cDNA clone encoding a hydrophobin protein was identified in a Dupont EST library of *Talaromyces thermophilus*. The *Talaromyces thermophilus* EST sequences were analyzed by conducting BLAST (Basic Local Alignment Search Tool; Altschul et al. (1993) *J. Mol. Biol.* 215:403-410; see also the explanation of the BLAST alogarithm on the world wide web site for the National Center for Biotechnology Information at the National Library of Medicine of the National Institutes of Health) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences of the *Talaromyces thermophilus* library were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

cDNA clone ftd1c.pk001.f12 encoded a polypeptide recognizable through the above analysis as a hydrophobin. The encoded protein, representing the precursor hydrophobin protein (SEQ ID NO:3), had a pLog score of 17.08 when compared with the encoded hydrophobin from *Aspergillis fumigatus* having Accession #AAB07707, and the same score of 17.08 with the hydrophobin precursor rodlet protein of *Aspergillis fumigatus* having Accession #P41746. The encoded protein had a pLog score of 16.89 when compared with the hydrophobin rodlet protein of *Emericella nidulans* having Accession #P28346. The encoded protein had a pLog score of 13.4 when compared to each of the hydrophobins of *Neosartorya aurata* (Accession MC13527), *Neosartorya spinosa* (Accession MC13538), *Neosantorya stramenia* (Accession MC13539), *Neosartorya fennelliae* (Accession MC1 3529), and *Neosartorya spathylata* (Accession MC13536).

Each of the sequences of the *Aspergillus nidulans*, *Emericella nidulans*, and TT1 hydrophobins was analyzed using the SignalP program (Nielsen, H et al., *Protein Engineering* 10, 1-6 (1997), to identify the junction between the secretion signal peptide and the mature protein. The signal peptides were removed prior to analysis for sequence alignment and percent identities. The mature protein amino acid sequences (SEQ ID NOs:1, 5, 6, 7) were aligned using the emma program of the emboss bioinformatics suite ((Rice, P. Longden, I. and Bleasby, A. "EMBOSS: The European Molecular Biology Open Software Suite" Trends in Genetics June 2000, vol 16, No 6. pp. 276-277); FIG. 2). The emma multiple sequence alignment was performed using the Clustal W method of alignment (Thompson, J. D., Higgins, D. G. and Gibson, T. J. (1994) Nucleic Acids Research, 22:4673-4680). The "default parameters" set for the emma program correspond to GAP PENALTY=10 and GAP EXTENSION PENALTY=5, and for pairwise alignments of proteins they are KTUPLE 1, GAP PENALTY=3, WINDOW=5 and DIAGONALS SAVED=5. Percent amino acid identities were determined using the infoalign program, also of the emboss suite of programs. Results are given in Table 1.

TABLE 1

Percent identities of amino acid sequence of mature TT1 to mature proteins of or encoded by closest BLAST hits

| Organism | Accession # | % identitiy |
|---|---|---|
| *Aspergillis fumigatus* | AAB07707 | 44.1 |
| *Aspergillis fumigatus* | P41746 | 43.4 |
| *Emericella nidulans* | P28346 | 43.8 |

Though the percent identities between the protein encoded by the EST of ftd1C.pk100.f12 and known hydrophobins were low as shown in Table 1, the protein encoded by the EST of ftd1C.pk001.f12 was conclusively identified as a hydrophobin by its size and the pattern of 8 highly conserved cysteines that are positioned within the mature protein in a 1-2-1-1-2-1 pattern (dashes represent variable numbers of amino acids; FIG. 1), that exists in all known hydrophobins. The mature TT1 protein was found to be 135 amino acids long, which is of similar size to known hydrophobins. This hydrophobin from *Talaromyces thermophilus* was named TT1.

TT1 was determined to be a Class I hydrophobin based on the size of the amino acid segments that intervene between the conserved cysteines. In Class II hydrophobins, all of the intervening amino acid segments represented by the dashes in the 1-2-1-1-2-1 cysteine pattern are of similar size. This size generally ranges between 8 and 16 amino acids. In Class I hydrophobins, the size of the first, third, fourth and fifth amino acid segments are a bit more variable, generally ranging from 5 to 18 amino acids. A distinguishing feature of Class I hydrophobins is that the second amino acid segment is much larger, generally about 25 amino acids long. TT1 has the larger second segment, thereby belonging in Class I.

Example 2

Partial Purification of TT1 from Fungal Expression Cultures

TT1 was expressed in a *Trichoderma reesei* expression system using a chimeric gene construction containing the following components, in the following order:
1) the promoter from the *Trichoderma* cbh1 (cellulase) gene
2) the polynucleotide encoding the secretion signal peptide of the cbh1 precursor protein
3) the polynucleotide encoding the mature TT1 protein with no translation stop codon
4) a polynucleotide encoding the Flag octapeptide and a His (6×) tag, incorporated to facilitate screening of fungal transformants and to aid in purification, followed by a translation stop codon
5) the transcription termination sequence from the cbh1 gene Expression of the cbh1 promoter was induced by growth on cellulose-containing medium for 5-6 days. Mycelia and culture medium were separated by centrifugation. The culture medium, in samples of 100 ml, was mixed at maximum speed for 2 min using the PT 1297/2 mixing head of a KINEMATICA Polytron PT 120 C (KINEMATICA AG, Littau-Lucerne, Switzerland). The samples were centrifuged at 5000 rpm for 3 min at 20° C. using a Sorvall GS-3 rotor. The resulting foam cake was collected. The mixing, centrifugation, and collection of foam were repeated. The foam samples were collected and lyophilized overnight, then dissolved in water. The dissolved protein was desalted on Bio-Rad 10 DG columns using 15 mM ammonium acetate at pH 7.5. The samples were then lyophilized.

Example 3

TT1 Coating of Films and Surfaces

For all TT1 coating studies, lyophilized powder of TT1 protein sample was suspended in a small volume of trifluoroacetic acid. The solution was evaporated to dryness and then resuspended and diluted in degassed water to an estimated concentration of 16 µg/ml. This concentration was based on the estimate that the TT1 protein sample contained TT1 as 10% of the total protein in the sample, as determined by visual inspection of a coomasie stained sample that was separated by gel electrophoresis. The total protein concentration was determined using the Bicinchoninic Acid Protein Assay Kit (Sigma, procedure No. TPRO-562).

The following polymer sheets and films were used for coating:

Fluoropolymers:
Teflon® PFA 1000LP: a copolymer of tetrafluoroethylene/-perfluoro(propyl vinyl ether), with a thickness of 250 µm (DuPont Company, Wilmington, Del.).
Teflon® FEP 1000A: a copolymer of tetrafluoroethylene and hexafluoropropylene, with a thickness of 250 µm (DuPont Company, Wilmington, Del.).
Teflon® PTFE 7A: a polytetrafluoroethylene homopolymer film (DeWal Industries, Inc. Narragansett, R.I.).
Tedlar® TR10SG3: a polyvinyl fluoride transparent film with high gloss that is 25 µm thick and has moderate polymer alignment (DuPont Company, Wilmington, Del.).
Tedlar® TR15BG5: a polyvinyl fluoride transparent film with high gloss that is 37.5 µm thick and has low polymer alignment (DuPont Company, Wilmington, Del.).
Nafion® NF 112: a perfluorosulfonic acid/polytetrafluoroethylene copolymer in the acid form, with a film thickness of 51 µm (DuPont Company, Wilmington, Del.).
Teflon® AF2400: a copolymer film of tetrafluoroethylene/perfluoro-2,2-dimethyl-1,3-dioxole (DuPont Company, Wilmington, Del.).

Polyolefins:
Tyvek® 8740D: a sheet of heat and pressure bonded high density polyethylene fibers, with 8740D designating a basis weight of 2.00 oz/yd$^2$ and 7.5 mils (a mil is 0.001 inch) thickness (DuPont Company, Wilmington, Del.).
Bynel® 38E536: an anhydride modifier, ethylene vinyl acetate based polymer adhesive (DuPont Company, Wilmington Del. USA) prepared as a film by standard methods.
Polypropylene PP6D81 resin (Dow Chemical Company, Midland, Mich.) prepared as a film by standard methods.
LDPE DPE1645: a low density polyethylene homopolymer made using a high pressure autoclave process, with melt index of 4 g/10 min and density of 0.923 g/cc prepared as a film by standard methods.

Ethylene Copolymer:
Surlyn® 1706 packaging resin (zinc ionomer, melt flow index 0.65 d/min by ASTM D1238, condition 190° C./2.16 kg) prepared as a film by standard methods.

Polyesters:
Sorona® 3GT PA585 film of 4 mm thickness extruded at 240° C. from poly(trimethylene terephthalate) prepared from dimethyl terephthalate and 1,3-propanediol at a ratio of 1.4:1 using Tyzor® TPT (DuPont Company, Wilmington, Del.) as transesterification catalyst.
Mylar®: a biaxially oriented, thermoplastic film made from ethylene glycol and dimethyl terephthalate (DuPont Company, Wilmington, Del.).

Polyamide:
Kevlar®/Nomex® 7550-5; a composition film of Kevlar® and
Nomex® as sold in the Thermount® line (DuPont Company, Wilmington, Del.) having 80% Kevlar® and 20% Nomex®.

Polyimide:
Kapton®: a film of polyimide polymer resulting from polycondensation reaction between pyromellitic dianhydride and 4,4.diaminodiphenyl ether (DuPont Company, Wilmington, Del.).

Samples of the polymer sheets and films described above (0.8 mm×22mm; see Table 2) were cleaned by ethanol and water washing, then immersed in solution containing TT1 protein sample with approximately 16 µg/ml of TT1 for 16 hours at room temperature. Following immersion in TT1 protein sample solution, samples were removed, rinsed with distilled water and air dried. The water contact angle (WCA) was determined on the coated air-dried composite structure. Surface hydrophobicity or hydrophilicity was determined via WCA measurements using the sessile drop technique as described in van der Mei, H. C. et al. 1991, Microbial Cell Surface Analysis, pp. 261-267, edited by D. S. Mozes et al., VCH, New York, using a Krus DSA MK2 instrument and a drop shape analysis software program (version 1.7; Kruss GmbH, Hamburg, Germany). Water contact angle (WCA) measurements were determined for all TT1 coated surfaces and controls immersed in water only (Table 2).

The difference (ΔC) in WCA between the untreated (no TT1 protein sample control) and TT1 treated samples was quite large (ΔC>200 up to 64°) for many surfaces including Teflon® and Tedlar® Fluoropolymers, Tyvek®, Bynel®, Surlyn®, Sorona®, polypropylene, and polyethylene (LDPE). With some surfaces, e.g., Kevlar®/Nomex®, Nafion®, Kapton®, and Mylar®, the difference in WCA between untreated and TT1 protein sample treated was low: ΔC was 20° or less. Although there was not a direct correlation, in general, materials with lower starting WCAs were altered less in their WCAs following TT1 protein sample treatment (with Nafion® providing an exception). From these examples, it was concluded that TT1 protein sample surface coverage was strongly influenced by the surface it was exposed to. These results demonstrated that the surface coverage, and therefore the change in hydrophilicity, was very good for Teflon® and Tedlar® Fluoropolymers, Tyvek®, Bynel®, Surlyn®, Sorona®, polypropylene, and polyethylene (LDPE).

TABLE 2

TT1 Hydrophobin Coating to DuPont Films and Surfaces

| Polymer | | Untreated WCA | TT1 Hydrophobin-Coated Polymer WCA | (Δ C.) |
|---|---|---|---|---|
| Class | Product | | | |
| Fluoropolymers | Teflon® PFA 1000LP | 110° | 50° | 60° |
| | Teflon® FEP 1000A | 106° | 53° | 53° |
| | Teflon® PTFE 7A | 103° | 53° | 50° |
| | Tedlar® TR10SG3 | 93° | 57° | 36° |
| | Tedlar® TR15BG5 | 75° | 54° | 21° |
| | Nafion® NF112 | 90° | 70° | 20° |
| | Teflon® AF2400 | 114° | 50° | 64° |
| Polyolefins | Tyvek® 8740D | 98° | 54° | 41° |
| | Bynel® 38E536 | 102° | 58° | 44° |
| | Surlyn® 1706 | 80° | 44° | 36° |
| | Polypropylene PP6D81 | 85° | 43° | 42° |
| | LDPE DPE1645 | 91° | 53° | 38° |
| Polyesters | Sorona® 3GT PA585 | 75° | 44° | 31° |
| | Mylar® | 77° | 59° | 18° |
| Polyamides | Kevlar®/Nomex® 7550-5 | 72° | 62° | 10° |
| Polyimides | Kapton® | 73° | 60° | 13° |

Example 4

Immersion Temperature Effect on TT1 Surface Coating and Stability

Samples of Teflon® PFA sheets (0.8 mm×22 mm) were immersed in solution containing TT1 protein sample with approximately 16 μg/ml of TT1 protein (prepared as described above) for 16 hours at temperatures ranging from room temperature to 80° C. as in Table 3. Following immersion in TT1 protein sample solution, washing and air drying, WCA's were determined and then all samples were heated at 90° C. for 24 hours. Subsequent to heating at 90° C., the TT1 coating stability was tested by washing with warm tap water for 5 minutes, drying and measuring the WCA of the surfaces again. As shown in Table 3, increasing the immersion temperature lowered the WCA of the TT1 coated Teflon® PFA which indicated better hydrophobin surface coverage. The sample immersed at room temperature showed a large increase in WCA following the 90° C. heating and warm water wash: ΔC=+420. This increase in WCA indicated that the protein coating applied at room temperature was unstable to heat treatment and warm water washing. The TT1 coating applied at room temperature was also shown to be unstable to warm water washing only. All samples initially immersed at elevated temperatures showed increased stability to 90° C. heating and warm water washing. Immersion at temperatures between 35° C. and 60° C. showed decreased WCAs, with the ΔCs ranging between −5° and −8°. Immersion at 80° C. followed by 90° C. heating and warm water washing actually showed a slight increase in WCA (ΔC=+2°). These results demonstrated that elevated temperature improved the surface coating and stability of TT1 coated Teflon® PFA.

TABLE 3

Effect of Immersion Temperature and Dry Heat Treatment on TT1 Coating of Teflon® PFA 1000LP

| Initial Coating Immersion Temp | WCA | 90° C./24 hr + warm water wash WCA | Δ C. |
|---|---|---|---|
| 25° C. | 54° | 96° | +42° |
| 35° C. | 49° | 41° | −8° |
| 45° C. | 47° | 42° | −5° |
| 50° C. | 47° | 42° | −5° |
| 60° C. | 49° | 42° | −7° |
| 80° C. | 46° | 48° | +2° |

Example 5

Elevated Temperature and Rate Improvement of TT1 Coating of Teflon® PFA

Teflon® PFA sheets (0.8 mm×22 mm) were immersed in solution containing TT1 protein sample with approximately 16 μg/ml TT1 protein (prepared as described above) at the following temperatures: 25° C. (room temperature), 40° C., 60° C. and 80° C. Immersion was for 3, 6 or 16 hours. Following immersion in TT1 protein sample solution, water washing at room temperature and air drying, WCA measurements were determined for all TT1 coated samples. In FIG. 3, the WCA for each time point is plotted against increasing temperature. For each immersion time, the WCA values decreased with increasing temperature. From this data it was concluded that elevated immersion temperature improved the rate and extent of TT1 coating of Teflon® PFA, and this occurred at each incubation time. Thus, the ability to treat surfaces with this thermophilic hydrophobin at elevated temperatures improves the coating and material surface property, as measured by the WCA.

Example 6

Stability of TT1 Coated Teflon® PFA and Sorona® 3GT

Three sheets each of TT1 coated Teflon® PFA and TT1 coated Sorona® 3GT were prepared by immersion in solution containing TT1 protein sample with approximately 16 μg/ml of TT1 protein (prepared as described above) for 16 hours at 40° C. The TT1 coated Teflon® PFA sheets were further heated at 90° C. for 24 hr. The WCA was measured for each TT1 coated sheet. A sheet each of TT1 coated Teflon® PFA and TT1 coated Sorona® 3GT was then subjected to one of the following test treatments: (i) washed with warm tap water for 5 min. (ii) heated in a 2% sodium dodecylsulfate (SDS) solution at 90°-100° C. for 10 min, or (iii) treated with sticky tape as an abrasive. For (iii), invisible tape (3M) was applied by pressing onto the TT1 coated surface and then removing. WCA measurements were determined for all TT1 coated sheets after test treatment.

The change in WCA for TT1 coated Sorona® 3GT was less than 15° after warm water washing, hot detergent treatment, and sticky tape treatment which indicated stability of the coating on this surface under these treatments. TT1 coated The change in WCA for TT1 coated Teflon® PFA was less than 10° after warm water washing, which indicated stability to this treatment. These results show that TT1 coating stability and robustness is strongly influenced by the surface on which it is aggregated or polymerized. Sorona® 3GT was found to be a particularly good surface for stability of TT1 coating.

TABLE 4

Stability of Hyrophobin Coated Teflon ® PFA and Sorona ® 3GT

| | Increase in WCA and Stability after Test Treatment | |
| --- | --- | --- |
| Test Treatment | TT1 coated Teflon ® PFA | TT1 coated Sorona ® 3GT |
| Warm water wash | 7° Yes[a] | 5° Yes |
| SDS/90-100° C. | 48° No[b] | 13° Yes |
| Sticky tape | 60° No | 4° Yes |

[a]Yes: Stable; WCA increase <15°
[b]No: Unstable; WCA increase >20°

The invention claimed is:

1. An isolated polynucleotide comprising:
    (a) a nucleotide sequence encoding a hydrophobin polypeptide, wherein the polypeptide has an amino acid sequence of at least 80% sequence identity when compared to SEQ ID NO: 1, is stable at 90° C., and wherein a surface coated with the polypeptide demonstrates a change in water contact angle of at least 20° when compared to an uncoated surface, or
    (b) the complement of the nucleotide sequence of (a), wherein the complement and the nucleotide sequence consist of the same number of nucleotides and are 100% complementary.

2. The polynucleotide of claim 1, wherein the amino acid sequence of the polypeptide has at least 85% sequence identity when compared to SEQ ID NO: 1.

3. The polynucleotide of claim 1, wherein the amino acid sequence of the polypeptide has at least 90% sequence identity when compared to SEQ ID NO: 1.

4. The polynucleotide of claim 1, wherein the amino acid sequence of the polypeptide has at least 95% sequence identity when compared to SEQ ID NO: 1.

5. The polynucleotide of claim 1, wherein the amino acid sequence of the polypeptide comprises SEQ ID NO: 1.

6. The polynucleotide of claim 1 wherein the nucleotide sequence comprises SEQ ID NO: 2.

7. A vector comprising the polynucleotide of claim 1.

8. A recombinant DNA construct comprising the polynucleotide of claim 1 operably linked to a secretion signal peptide coding sequence and at least one regulatory sequence.

* * * * *

SEQUENCE LISTING

<160> NUMBER OF SEQ ID NOS: 7

<210> SEQ ID NO 1
<211> LENGTH: 135
<212> TYPE: PRT
<213> ORGANISM: Talaromyces thermophilus

<400> SEQUENCE: 1

```
Leu Pro Asn Val Gly Pro Ser Gly Lys Thr Ala His Lys Pro His Gln
1               5                   10                  15

Glu Pro Phe Trp Pro Val Gln Gln Asp Val Thr Val Glu Gln Ala Lys
            20                  25                  30

Ala Ile Cys Gly Glu Gly Asn Gln Val Ala Cys Cys Asn Glu Val Ser
        35                  40                  45

Tyr Ala Gly Asp Thr Thr Glu Ile Ala Thr Gly Pro Leu Ala Gly Thr
    50                  55                  60

Leu Lys Asp Leu Leu Gly Gly Lys Asn Gly Ala Lys Gly Leu Gly Leu
65                  70                  75                  80

Phe Asp Lys Cys Ser Arg Leu Asn Val Asp Leu Leu Gly Leu Ser
                85                  90                  95

Ser Leu Ile Asn Gln Glu Cys Lys Gln His Ile Ala Cys Cys Gln Gly
                100                 105                 110

Asn Glu Ala Asp Ser Ser Asn Asp Leu Ile Gly Leu Asn Ile Pro Cys
            115                 120                 125

Ile Ala Leu Gly Ser Leu Leu
        130             135
```

<210> SEQ ID NO 2
<211> LENGTH: 405
<212> TYPE: DNA
<213> ORGANISM: Talaromyces thermophilus

<400> SEQUENCE: 2

```
ctgccaaacg tcggtcccag tgggaagacg gctcacaagc cgcaccagga gcctttctgg    60
cctgtgcagc aggacgtgac cgtggaacag gccaaggcta tctgtggtga aggcaaccag   120
gtcgcttgct gcaacgaggt cagctacgcg ggcgacacca ccgaaatcgc gaccggcccc   180
ctggctggca ccctcaagga cctgctcggc ggcaagaacg gcgccaaggg cctgggtctc   240
```

```
ttcgacaagt gctcgcgtct caatgtcgat ctcctgcttg gcctgtcgag cctcatcaac    300
caagaatgca agcagcacat tgcctgctgc agggcaacg aggccgattc ctccaacgac     360
ctcatcggtc tcaacattcc ttgcattgcc cttggctcgc tgctg                    405
```

<210> SEQ ID NO 3
<211> LENGTH: 151
<212> TYPE: PRT
<213> ORGANISM: Talaromyces thermpohilus

<400> SEQUENCE: 3

```
Met Lys Phe Ala Gly Val Leu Leu Ala Val Ala Ala Ala Thr Ala
1               5                   10                  15

Leu Pro Asn Val Gly Pro Ser Gly Lys Thr Ala His Lys Pro His Gln
                20                  25                  30

Glu Pro Phe Trp Pro Val Gln Gln Asp Val Thr Val Glu Gln Ala Lys
            35                  40                  45

Ala Ile Cys Gly Glu Gly Asn Gln Val Ala Cys Cys Asn Glu Val Ser
        50                  55                  60

Tyr Ala Gly Asp Thr Thr Glu Ile Ala Thr Gly Pro Leu Ala Gly Thr
65                  70                  75                  80

Leu Lys Asp Leu Leu Gly Gly Lys Asn Gly Ala Lys Gly Leu Gly Leu
                85                  90                  95

Phe Asp Lys Cys Ser Arg Leu Asn Val Asp Leu Leu Leu Gly Leu Ser
            100                 105                 110

Ser Leu Ile Asn Gln Glu Cys Lys Gln His Ile Ala Cys Cys Gln Gly
        115                 120                 125

Asn Glu Ala Asp Ser Ser Asn Asp Leu Ile Gly Leu Asn Ile Pro Cys
    130                 135                 140

Ile Ala Leu Gly Ser Leu Leu
145                 150
```

<210> SEQ ID NO 4
<211> LENGTH: 453
<212> TYPE: DNA
<213> ORGANISM: Talaromyces thermophilus

<400> SEQUENCE: 4

```
atgaagttcg ccggtgtctt gcttgctgtc gccgctgcgg cgactgccct gccaaacgtc    60
ggtcccagtg gaagacggc tcacaagccg caccaggagc ctttctggcc tgtgcagcag    120
gacgtgaccg tggaacaggc caaggctatc tgtggtgaag caaccaggt cgcttgctgc    180 aacgaggtca gctacgcggg cgacaccacc gaaatcgcga ccggccccct ggctggcacc    240
ctcaaggacc tgctcggcgg caagaacggc gccaagggcc tgggtctctt cgacaagtgc    300
tcgcgtctca atgtcgatct cctgcttggc ctgtcgagcc tcatcaacca gaatgcaag    360 cagcacattg cctgctgcca gggcaacgag gccgattcct ccaacgacct catcggtctc    420
aacattcctt gcattgccct ggctcgctg ctg                                  453
```

<210> SEQ ID NO 5
<211> LENGTH: 141
<212> TYPE: PRT
<213> ORGANISM: Aspergillus fumigatus

<400> SEQUENCE: 5

```
Leu Pro Gln His Asp Val Asn Ala Ala Gly Asn Gly Val Gly Asn Lys
1               5                   10                  15
```

Gly Asn Ala Asn Val Arg Phe Pro Val Pro Asp Asp Ile Thr Val Lys
            20                  25                  30

Gln Ala Thr Glu Lys Cys Gly Asp Gln Ala Gln Leu Ser Cys Cys Asn
        35                  40                  45

Lys Ala Thr Tyr Ala Gly Asp Val Thr Asp Ile Asp Glu Gly Ile Leu
    50                  55                  60

Ala Gly Thr Leu Lys Asn Leu Ile Gly Gly Ser Gly Thr Glu Gly
65                  70                  75                  80

Leu Gly Leu Phe Asn Gln Cys Ser Lys Leu Asp Leu Gln Ile Pro Val
                85                  90                  95

Ile Gly Ile Pro Ile Gln Ala Leu Val Asn Gln Lys Cys Lys Gln Asn
            100                 105                 110

Ile Ala Cys Cys Gln Asn Ser Pro Ser Asp Ala Ser Gly Ser Leu Ile
        115                 120                 125

Gly Leu Gly Leu Pro Cys Ile Ala Leu Gly Ser Ile Leu
    130                 135                 140

<210> SEQ ID NO 6
<211> LENGTH: 141
<212> TYPE: PRT
<213> ORGANISM: Aspergillus fumigatus

<400> SEQUENCE: 6

Leu Pro Gln His Asp Val Asn Ala Ala Gly Asn Gly Val Gly Asn Lys
1               5                   10                  15

Gly Asn Ala Asn Val Arg Phe Pro Val Pro Asp Asp Ile Thr Val Lys
            20                  25                  30

Gln Ala Thr Glu Lys Cys Gly Asp Gln Ala Gln Leu Ser Cys Cys Asn
        35                  40                  45

Lys Ala Thr Tyr Ala Gly Asp Val Thr Asp Ile Asp Glu Gly Ile Leu
    50                  55                  60

Ala Gly Thr Leu Lys Asn Leu Ile Gly Gly Ser Gly Thr Glu Gly
65                  70                  75                  80

Leu Gly Leu Phe Asn Gln Cys Ser Asn Val Asp Leu Gln Ile Pro Val
                85                  90                  95

Ile Gly Ile Pro Ile Gln Ala Leu Val Asn Gln Lys Cys Lys Gln Asn
            100                 105                 110

Ile Ala Cys Cys Gln Asn Ser Pro Ser Asp Ala Ser Gly Ser Leu Ile
        115                 120                 125

Gly Leu Gly Leu Pro Cys Ile Ala Leu Gly Ser Ile Leu
    130                 135                 140

<210> SEQ ID NO 7
<211> LENGTH: 139
<212> TYPE: PRT
<213> ORGANISM: Emericella nidulans

<400> SEQUENCE: 7

Leu Pro Pro Ala His Asp Ser Gln Phe Ala Gly Asn Gly Val Gly Asn
1               5                   10                  15

Lys Gly Asn Ser Asn Val Lys Phe Pro Val Pro Glu Asn Val Thr Val
            20                  25                  30

Lys Gln Ala Ser Asp Lys Cys Gly Asp Gln Ala Gln Leu Ser Cys Cys
        35                  40                  45

Asn Lys Ala Thr Tyr Ala Gly Asp Thr Thr Val Asp Glu Gly Leu
    50                  55                  60

-continued

```
Leu Ser Gly Ala Leu Ser Gly Leu Ile Gly Ala Gly Ser Gly Ala Glu
65                  70                  75                  80

Gly Leu Gly Leu Phe Asp Gln Cys Ser Lys Leu Asp Val Ala Val Leu
                85                  90                  95

Ile Gly Ile Gln Asp Leu Val Asn Gln Lys Cys Lys Gln Asn Ile Ala
            100                 105                 110

Cys Cys Gln Asn Ser Pro Ser Ser Ala Asp Gly Asn Leu Ile Gly Val
        115                 120                 125

Gly Leu Pro Cys Val Ala Leu Gly Ser Ile Leu
    130                 135
```